United States Patent [19]

Huchette et al.

[11] Patent Number: 4,766,070
[45] Date of Patent: Aug. 23, 1988

[54] FERMENTATION PROCESS AND SUBSTRATE

[75] Inventors: Michel Huchette; Francis Devos, both of Merville, France

[73] Assignee: Roquette Freres, France

[21] Appl. No.: 935,636

[22] Filed: Nov. 25, 1986

Related U.S. Application Data

[63] Continuation of Ser. No. 734,815, May 16, 1985, abandoned, which is a continuation of Ser. No. 555,448, Nov. 28, 1983, abandoned, which is a continuation of Ser. No. 331,812, Dec. 17, 1981, abandoned.

[30] Foreign Application Priority Data

Dec. 19, 1980 [FR] France ............................... 80 27143

[51] Int. Cl.⁴ .............................................. C12P 21/04
[52] U.S. Cl. ...................................... 435/71; 435/202; 435/222; 435/253
[58] Field of Search ................. 435/32, 202, 222, 253, 435/836, 839, 71; 426/489, 495

[56] References Cited

U.S. PATENT DOCUMENTS 2,530,210  11/1950  Smythe ............................... 435/222
2,594,308   4/1952  Heisler et al. ....................... 426/489

FOREIGN PATENT DOCUMENTS 2637810  2/1978  Fed. Rep. of Germany ...... 426/489
0042473  4/1977  Japan .................................. 426/495

OTHER PUBLICATIONS

Micq et al., "Vegetable Water From Potatoes as Nutritive Medium in a Fermentation Process" Chem. Abstracts, vol. 53 (1959), p. 641.

Talburt et al., "Potato Processing" 3rd edition (1975), Avi Publishing Co., pp. 546 & 555–556.

Holnicki, "Use of Proteins Obtained from Potato Juice" Chem. Abstracts (1968), vol. 71, p. 215, Abstract No. 11912r.

*Primary Examiner*—R. B. Penland
*Attorney, Agent, or Firm*—Larson and Taylor

[57] ABSTRACT

The invention relates to a fermentation process. This process is characterized by the fact that recourse is had, as a proteinic nutrient substance introduced into the fermentation medium, to an effective amount of potato protein obtained by coagulation from red waters.

1 Claim, No Drawings

FERMENTATION PROCESS AND SUBSTRATE

The present application is a continuation of application Ser. No. 734,815 filed May 16, 1985; which is a continuation of Ser. No. 555,448 of Nov. 28, 1983; which is a continuation of parent application Ser. No. 331,812 of Dec. 17, 1981 all abandoned.

The invention relates to a fermention process using a fermentation substrate which constitutes a novel industrial product.

By the expression "fermentation process" is meant any process intended for the production, by fermentation, of substances such as enzymes, organic acids, antibiotics, polysaccharides, amino acids or vitamins.

In the practising of these processes, recourse is had to fermentation media into which indispensable nutrient substances are introduced belonging to the group of carbohydrates, inorganic salts, oligo-elements, vitamins and proteinic materials introducing amino acids, polypeptides and proteins.

The proteinic materials used until now are generally constituted by soya cakes, yeasts and yeast extracts, soaking or steeping liquors from corn also called "corn-steep", blood flours, milk proteins, and "pharmamedia", generally giving satisfaction.

It is however an object of the invention to provide a process and a substrate of the type concerned leading to improved results notably from the point of view of fermentation yield and enabling the valorization of a raw material whose known applications do not exploit all the advantages.

Now, the Applicants have had the merit of finding that the potato protein obtained by coagulation from what is called red water or fruit water -a well-known by-product of starch factories obtained in the extraction of the starch and of the pulp from potato tubers- used as a proteinic nutrient substance, enabled the yield of certain fermentations to be considerably increased and procured a certain number of other advantages which will be discussed below.

The merit of the Applicants is all the greater since everything led to the belief that the application of the potato protein concerned would be inoperative particularly due to the fact that said protein is in completely insolubilized and denatured form and although it has already been known to use directly, as the protein source in fermentations, more or less concentrated or even partially deproteinized red waters as well moreover as powders containing, in soluble form, the same proteins, these powders having, for example, been obtained by spraying or atomization from concentrated red water.

The fermentation process according to the invention is therefore characterized by the fact that recourse is had, as a proteinic nutrient substance introduced into the fermentation medium, to an effective amount of potato protein obtained by coagulation of red water.

The fermentation substrate according to the invention is characterized by the fact that it contains, as a proteinic substance, an effective amount of potato protein obtained by coagulation of red water.

Finally, the invention is directed, as a novel use of potato protein obtained by coagulation of red water, at the utilization of the latter in the constitution of the fermentation substrate.

The invention also encompasses a certain number of other features which are preferably used at the same time and which will be more explicitly considered below.

The invention will be well understood by means of the additional description which follows as well as of the examples, both given particularly with respect to advantageous embodiments.

In order therefore to carry out fermentations, procedure is as follows or in equivalent manner, but by having recourse, as a proteinic material indispensable for the good progress of the fermentation, to an effective amount of potato protein obtained by coagulation from red waters.

The "effective amount" represents the quantity of potato protein used according to the invention by which is introduced a quantity of true protein corresponding to the quantity of true protein, known by itself which is introduced by the conventional protein sources.

The coagulation of the protein from red water can be carried out thermically, chemically or thermochemically.

This protein contains more than 70% of protein reckoned as $N \times 6.25$ on dry matter and more generally, from 72 to 95% of proteins.

By thermochemical coagulation, a product is obtained giving satisfaction and having, after drying and grinding, in fine powder form, a gray to greenish color, of which a typical composition is as follows:

| | |
|---|---|
| water | 8 to 9% |
| proteins (N × 6.25) | 75 to 82% |
| residue of calcination | 1 to 3% |
| aqueous extract | 3 to 7% |
| sulfuric ether extract | 4 to 6% | the sulfuric ether extract being constituted for the most part by fatty acids. The proportion of certain of these fatty acids may be as follows:

| | |
|---|---|
| lauric acid | 1% |
| myristic acid | 1% |
| palmitic acid | 27% |
| stearic acid | 7% |
| oleic acid | traces |
| linoleic acid | 60% |

The distribution of the various amino acids constituting this protein, can be established as follows:

| Acids | % by weight of amino nitrogen |
|---|---|
| aspartic acid | 12.6 |
| glutamic acid | 10.2 |
| alanine | 4.6 |
| arginine | 4.8 |
| cystine | 1.5 |
| glycine | 4.8 |
| histidine | 1.8 |
| isoleucine | 5.9 |
| leucine | 10.0 |
| lysine | 7.5 |
| methionine | 22.1 |
| phenylalanine | 6.2 |
| proline | 4.8 |
| serine | 5.3 |
| threonine | 5.7 |
| tyrosine | 5.2 |
| valine | 7.0 |

To obtain the abovesaid protein, procedure is for example as follows:

The red or fruit waters are brought to a pH of the order of 4.6 to 5.2 by the addition of an inorganic or organic acid, and then they are brought to a temperature sufficient, generally comprised between 90° and 110° C., to cause floculation of the proteins. This temperature is held for a sufficient time to complete the floculation, that is to say to deaerate the floculate and to free it from the liquid in which it is suspended; generally, this temperature is held for about 5 to 15 minutes. The floculate obtained is then separated, for example on a centrifugal decantor, and then dried in a pneumatic drier.

This protein represents only 25 to 30% approximately of the dry matter contained in the "red waters" and only contains a small amount of the essential biological constituents initially present in the red waters, whence an additional unfavorable prejudice against the use of this protein in fermentation processes.

Red waters occur when, in order to withdraw the starch and the pulp from the potatoes, the tubers are disintegrated in starch factories in such a way that their constituent cells are ground, the starch and the pulp being then separated from so-obtained gratings. The residual red or fruit waters so-obtained contain in solution the larger part of the constituents other than the starch and the pulp and hence include, besides proteins present in a preponderant amount very many compounds of very high biological value such as vitamins, inorganic materials, organic acids, sugars and fats.

The potato protein, besides enabling the yield of certain fermentations to be particularly increased, brings the following important advantages to the latter:
much easier sterilization of the fermentation medium, lower viscosity of the fermentation medium, whence greater ease of stirring and aeration,
purification of culture worts facilitated,
reduction in pollution, which will be discussed in more detail below.

Thus, for example, yields increased of more than 50% can be obtained in α-amylase production, when replacing the soya protein conventionally used by coagulated potato protein.

The richness in true protein of the protein used according to the invention being approximately double that of soya cakes the same nitrogen ratios can be obtained by application at a twice lower quantity. There results a much lower viscosity of the medium as well as much greater facility of aeration and stirring.

The purification of the culture worts is on the other hand easier considering the absence of inert material such as, for example, cellulosic material, whence a reduction in the loss of noble products in filtration cakes or in centrifugation slurries.

The potato protein which has, after grinding, a very fine granulometry, less than 200 $\mu$ and more generally less than 50 $\mu$, is dispersed very easily in water, which has the effect of facilitating sterilization of the medium.

Considering its process of production by heat coagulation and then drying in agro-food equipment, the product has on the other hand a very low bacteriological contamination level, which is a great advantage in fermentation processes.

The high fermentation yields obtained by means of the use of the potato protein finally result in better productivity of the equipment and enable considerable reduction in the pollution per biological unit produced.

The application of this potato protein in the fermentation process according to the invention or in the constitution of fermentation substrates is effected by introduction of the protein into the fermentation medium with stirring, all other features of the process being equivalent to those of already known processes.

The following examples relate to advantageous embodiments.

EXAMPLE 1

Production of bacterial α-amylase

Two fermenters $B_1$ and $B_2$ of the BIOLAFITTE type of 20 liters were provided with fermentation media containing:

|  | $B_1$ | $B_2$ |
| --- | --- | --- |
| malto-dextrin | 750 g | 750 g |
| $NH_4NO_3$ | 60 g | 60 g |
| potato protein | 590 g | 0 g |
| soya cakes | 0 g | 1 050 g |

The potato protein floculated by thermocoagulation applied was in the form of a very fine powder, 99% by weight of the particles having a size smaller than 50$\mu$; it had a loss on drying of 6.2% and titrated 84.9% of protein on the dry matter ($N \times 6.25$).

The residue on calcination of this protein was equal to 2.7%, the percentage of total lipids being 3.5% and the aqueous extract being equal to 6.0%, these three latter percentages being expressed on the commercial material as such.

The soya cakes used in the present example titrated about 48% of proteins ($N \times 6.25$).

The contents of the two fermenters were adjusted to 15 liters; they were seeded by means of 300 ml of a 48 hour preculture of *Bacillus Subtilis* cultivated on a medium containing 2% of yeast extracts and 5% of malto-dextrin.

The fermentation conditions inside the fermenters $B_1$ and $B_2$ were as follows:
aeration: 1 volume of air each minute, namely 22 1/minute,
stirring: 700 rpm,
temperature: 35° C.

Production of α-amylase was followed in each of the fermenters by measuring the activity by the RBU method (RAPIDASE Bacterial Unit). According to this method, the dextrinifying action of the bacterial amylases was estimated by measuring the time necessary for the appearance of a change in color to iodine of the substrate, this change corresponding to dextrinification of the latter. The RBU unit is defined as being the amount of enzyme which dextrinifies 1 mg of starch in 1 minute.

Table I below gives the results obtained.

TABLE I

| Fermentation time (H) | Activity in $B_1$ (in RBU) | Activity in $B_2$ (in RBU) |
| --- | --- | --- |
| 19 | 400 | 190 |
| 26 | 620 | 300 |
| 43 | 785 | 550 |
| 67 | 1 300 | 700 |

This experimentation was reproduced five times in sequence. The activities obtained after a time of 67 hours, in the course of these five experiments, are indicated in Table II.

TABLE II

| Test | Activity in $B_1$ (in RBU) | Activity in $B_2$ (in RBU) |
|---|---|---|
| 1 | 1 300 | 700 |
| 2 | 1 150 | 750 |
| 3 | 1 220 | 800 |
| 4 | 1 380 | 730 |
| 5 | 1 210 | 770 |

From the numerical results collected in Table II it appears that an average of 1 250 RBU is obtained by the use of potato protein and 750 RBU on soya; an increase in activity of 500 RBU is hence recorded, namely about 66.7% with respect to the activity obtained on soya.

Besides this very distinct improvement in activity, the use of potato protein has several other important advantages with respect to the use of soya cakes.

The viscosity of the fermentation medium is less in the fermenter $B_1$ which facilitates aeration.

The flocculation of bacterial bodies as well as the filtration are facilitated on the potato protein based medium. Thus, after heating to 50° C., the two media were filtered, after adjustment to 15 liters, on a laboratory Buchner filter. The filtration speed, brought back to 1 m2 of filtering surface, is equal to about 250 liters per m2 and per hour for the medium based on potato proteins, whereas it is only 180 liters per m2 and per hour for the soya based medium.

The weight of the wet cake was, on the other hand, three times greater in the case of the soya based medium than in the case of the potato protein based medium. The volume or the filtrate recovered was 14 liters for the first medium and 12 liters for the second medium.

EXAMPLE 2

Production of heat-resistant α-amylase

With the object of producing a heat-resistant α-amylase, a strain of *Bacillus Licheniformis* ATCC 6598 was cultivated in three different media contained in three separate fermenters and containing maltose syrup as a source of carbon as well as:
 soya flour, or
 heat coagulated potato protein,
 corn solubles and potato protein, as the source of nitrogen.

The culture of the micro-organism was carried out in all cases at 43° C. and the activity of the α-amylase produced was determined by the SKB method, as described in "Cereal Chemistry", 16, 172 (1939).

First fermenter

The *Bacillus Licheniformis* strain was cultivated in 2 liter Erlenmeyer flasks, placed on a rotary shaker operating at 220 rpm, these Erlenmeyer flasks containing 400 ml of a medium having the following composition:

| | |
|---|---|
| maltose syrup | 100 g/l |
| soya flour | 30 g/l |
| $Na_2HPO_412H_2O$ | 5 g/l |
| $KH_2PO_4$ | 1 g/l |
| lard oil | 0.5 ml/l |

After 30 hours of preculture, the 400 ml were introduced into a production fermenter of 20 liters, containing a medium of similar composition to that of the preculture.

The cultivation conditions were as follows:
 stirring: 1 200 rpm,
 aeration: 0.8 volume/minute,
 temperature: 43° C.,
 time: 120 hours,
 a starting pH equal to 6.7, then stabilization at pH 7.
The final activity measured was:

| |
|---|
| 4 140 SKB at 37° C. |
| 15 525 SKB at 85° C. |

Second fermenter

The same process as previously was applied, excepted the fact that the preculture and production media had the following composition:

| | |
|---|---|
| maltose syrup | 110 g/l |
| potato protein (identical with that of Example 1) | 15 g/l |
| $Na_2HPO_412H_2O$ | 5 g/l |
| $KH_2PO_4$ | 1 g/l |
| lard oil | 5 ml/l. |

The conditions were identical with those selected for the first fermenter.
The final activity measured was:

| |
|---|
| 5 000 SKB at 37° C. |
| 18 735 SKB at 85° C. | which corresponds to an increase in activity of about 20%, obtained merely by replacement of the soya flour by potato protein.

Third fermenter

The operational process as well as the culture conditions were the same as for the two preceding fermenters.

The culture medium here had the following composition:

| | |
|---|---|
| maltose syrup | 110 g/l |
| potato protein (identical with that of Example 1) | 15 g/l |
| corn steep liquors (corn steep liquid with 50% of dry matter) | 5 g/l |
| $Na_2HPO_4$ | 5 g/l |
| lard oil | 5 ml/l. |

The final activity measured was:

| |
|---|
| 5 000 SKB at 37° C. |
| 19 000 SKB at 85° C., | which corresponds to an activity almost equivalent to that obtained in the second fermenter.

EXAMPLE 3

Production of a neutral bacterial protease of *Bacillus Subtilis*

This example establishes a comparison between the yields obtained in the production of a neutral bacterial protease of *Bacillus Subtilis*, on the one hand, in a medium containing potato protein and, on the other hand, in a medium containing soya isolate.

Two 20 liter fermenters, containing about 15 liters of medium identified below, were thus prepared; the compositions of the two production media were as follows:

|  | Fermenter n° 1 | Fermenter n° 2 |
|---|---|---|
| Malto-dextrin of DE = 17 | 3 750 g | 3 750 g |
| $H_3PO_4$ | 62.5 ml | 62.5 ml |
| Soya protein<br>(N × 6.25 = 92%) | 525 g | — |
| Dry yeast<br>(N × 6.25 = 45%) | 37.5 g | 37.5 g |
| Corn steep liquor<br>(with 50% of dry matter) | 125 g | 100 g |
| Heat coagulated potato protein (79.2% N × 6.25) | — | 615 g |
| $(NH_4)_2HPO_4$ | 125 g | 125 g |
| $MgSO_4 7H_2O$ | 12.5 g | 12.5 g |
| $ZnSO_4$ | 0.5 g | 0.5 g |

Two precultures of 50 ml, i.e. about 0.33% seeding, established on preculture media of compositions respectively identical with those of the production media, served for seeding the two fermenters.

For the preparation of these inoculums and for the realization of the production process, the same culture parameters were used, namely:
pH: 6.9 to 7.2
temperature: 37° C.
aeration: 1 l air/1 l of medium/minute
stirring: 180 rpm Samples were taken from the two fermenters from the 16th hour in order to check the enzymatic activity, and this until obtaining of a constant activity for two to three hours.

The method of determining the enzymatic activity is based on the principle according to which the enzyme acting on the casein liberates hydrolysis products not precipitable by trichloroacetic acid, which gives a blue coloration with FOLIN reagent, which is measured by a spectrophotometer at 660 mµ. This method constitues a modification of the so-called ANSON method (J. Gen. Physiol. 22, 79 (1938), the casein being used as a substrate in place of the hemoglobin.

The results obtained in the two fermenters were as follows:

|  | Fermenter n° 1 | Fermenter n° 2 |
|---|---|---|
| fermentation time | 19 h | 18 h |
| titer on stopping | 27 500 units of activity/ml (caseinolytic power) | 31 000 units of activity/ml (caseinolytic power) |

The enzymatic activity obtained in the medium containing the potato protein is hence higher by about 10% than that obtained in the medium based on soya isolate.

EXAMPLE 4

Bacitracin production

The micro-organism used for the production of bacitracin is *Baccilus Licheniformis* deposited at the ATCC (American Type Culture Collection) under the n° 10 716.

This strain is preserved in a refrigerator in the form of a suspension of spores in a tryptone salt medium, supplemented with 15% of glycerin, or on a gelosed soya trypticase. In order to produce bacitracin in a fermenter of 20 liters, the following medium was inoculated with a suspension of spores, in an Erlenmeyer flask of 500 ml, containing 60 ml of a liquid medium with:
1% peptone,
1% yeast extract,
1% malto-dextrin of DE equal to 21-23.

This Erlenmeyer flask was placed on a shaker at 37° C. for 18 to 24 hours.

A subculture was then carried out in the same peptonized broth as previously indicated (Erlenmeyer flask of 5 l containing 500 ml), under identical conditions, for 6 hours.

Two 20 liter fermenters, containing media whose composition is indicated below, were then seeded with 200 ml of this subculture.

| Fermenter 1 | Fermenter 2 |
|---|---|
| 4% of soya flour | 2.5% potato protein (identical with that of Example 1) |
| 0.5% $CaCO_3$ | 0.5% $CaCO_3$ |
| 0.5% starch | 0.5% starch |

The conditions applied to the two fermenters were strictly identical, that is to say:
temperature: 37° C.
aeration: 1 volume/volume/minute
stirring: 500 rpm The fermentation time was 24 hours in both cases.

A bacitracin unit is defined by the antibiotic amount which, at a dilution of 1:1 024 in a culture broth (known by the name "beef infusia broth"), inhibits the growth of *Streptococcus hemolyticus* of group A, under the conditions defined in Biochemical Engineering (R. Steel, ed.) p. 185 —Mac Millan New York.

The results obtained in the case of two successive tests were as follows:

|  | Fermenter 1 | Fermenter 2 |
|---|---|---|
| first test | 328 units/ml | 385 units/ml |
| second test | 312 units/ml | 374 units/ml |

From a comparison of these figures, it is apparent that the use of potato protein improves therefore, here again, the production yields very distinctly.

I claim:

1. In a conventional fermentation process for the production of amylase, protease or bacitracin, wherein a fermentation medium comprising carbohydrates, inorganic salts, oligoelements, vitamins and proteinic materials is introduced into a fermentation vessel, the fermentation medium is seeded with a fermentation agent effective to produce amylase, protease or bacitracin, and fermentation conditions are established and maintained until the production of amylase, protease or bacitracin is achieved, the improvement consisting essentially of selecting as the proteinic material a protein obtained by coagulation from red waters and containing more than 70% protein calculated as N×6.25 on dry matter.

* * * * *